(12) United States Patent
Venkatragavan et al.

(10) Patent No.: US 11,760,750 B1
(45) Date of Patent: Sep. 19, 2023

(54) PROCESS FOR PREPARING LEVOKETOCONAZOLE

(71) Applicant: Nuray Chemicals Private Limited, Tamilnadu (IN)

(72) Inventors: Ramasamy Venkatragavan, Thiruvallur (IN); Senthilkumaran Paramanandam, Thiruvallur (IN); Jayakumar Ayyamuthu, Thiruvallur (IN); Andi Selvamani, Thiruvallur (IN); Sengodan Manickam, Thiruvallur (IN); Ravi Silambarasan, Thiruvallur (IN); Murugan Arunkumar, Thiruvallur (IN); Sorakka Pichandi Parthipan, Thiruvallur (IN)

(73) Assignee: Nuray Chemicals Private Limited, Tamilnadu (IN)

( * ) Notice: Subject to any disclaimer, the term of this patent is extended or adjusted under 35 U.S.C. 154(b) by 0 days.

(21) Appl. No.: 18/180,997

(22) Filed: Mar. 9, 2023

(30) Foreign Application Priority Data

May 18, 2022 (IN) .............................. 202241028677

(51) Int. Cl.
*C07D 405/06* (2006.01)
(52) U.S. Cl.
CPC ................................. *C07D 405/06* (2013.01)

(58) Field of Classification Search
CPC ................................................... C07D 405/06
See application file for complete search history.

(56) References Cited

U.S. PATENT DOCUMENTS 6,040,307 A   3/2000   Gray et al.

FOREIGN PATENT DOCUMENTS

WO   2006/0728881 A1   7/2006

OTHER PUBLICATIONS

Damps et al., Stereoselective Syntheses of Both Enantiomers of Ketoconazole from (R)- and (S)-Epichlorohydrin, Tetrahedron: Asymmetry (1995) 6(6): 1283-1294, 1995.
Heeres et al., Antimycotic Imidazoles. Part 4. Synthesis and Antifungal Activity of Ketoconazole, a New Potent Orally Active Broad-Spectrum Antifungal Agent, J. Med. Chem. (1979) 22(8): 1003-1005.
Rotstein et al., Stereoisomers of Ketoconazole: Preparation and Biological Activity' J. Med. Chem, 1992(35): 2818-2825.
United States Pharmacopoeia, Chapter <1174> Powder Flow (2012).
Wells, J. Chapter 8 (pp. 133-134) in Pharmaceutics: The Science of Dosage Form Design (M. E. Aulton ed., 2nd Ed. 2002).

*Primary Examiner* — Brenda L Coleman
(74) *Attorney, Agent, or Firm* — Merchant & Gould P.C.; Daniel R. Evans

(57) ABSTRACT

The present disclosure relates to a process for the preparing levoketoconazole, its salts, solvates, and solid-state forms thereof.

30 Claims, 2 Drawing Sheets

PROCESS FOR PREPARING LEVOKETOCONAZOLE

Related Application

Figure 1:
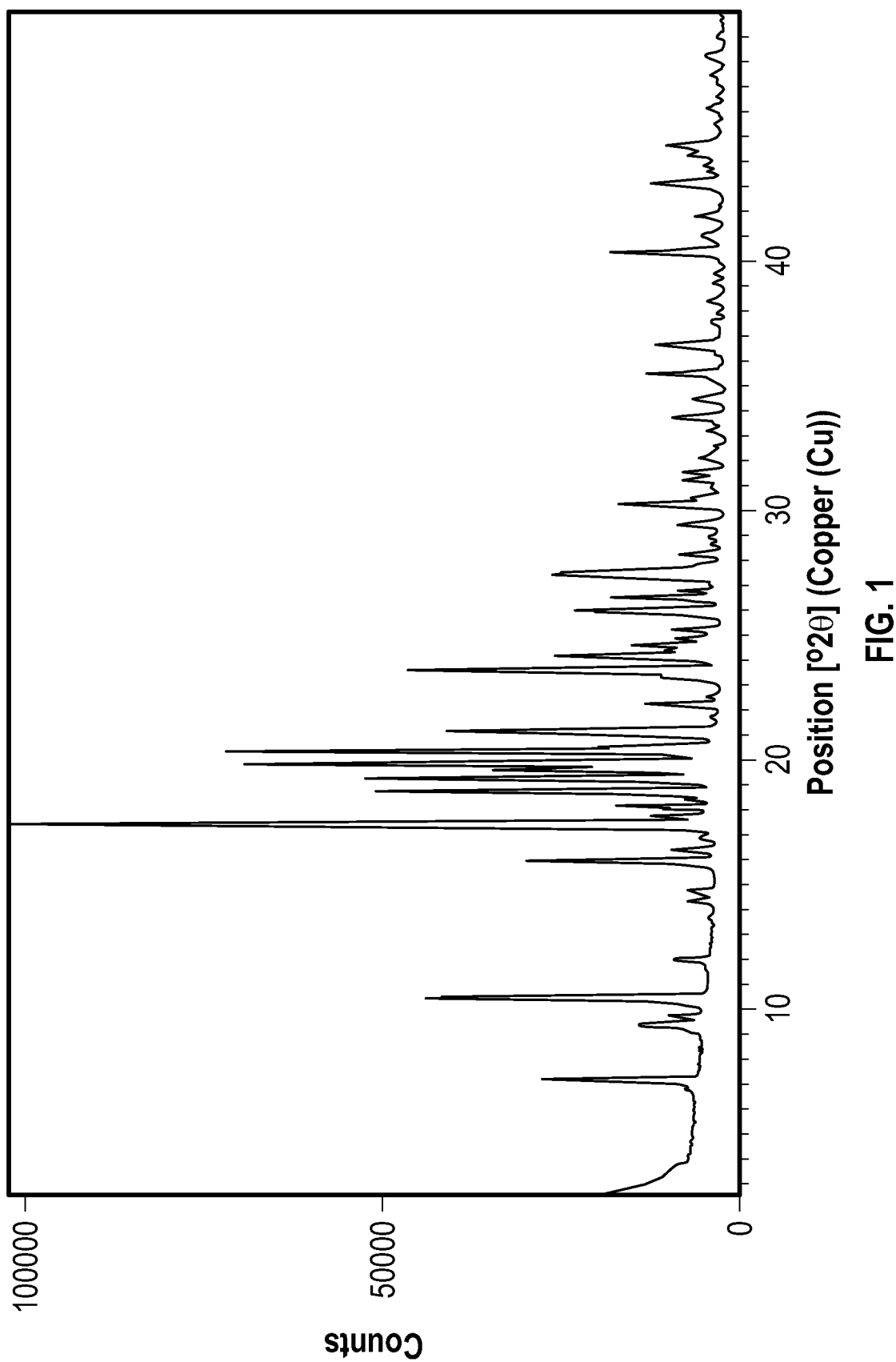

This application claims priority to Indian Patent Application number 202241028677, filed on May 18, 2022.

FIELD

The present disclosure relates to a process for preparing levoketoconazole, its salts, solvates, and solid-state forms thereof.

BACKGROUND

Levoketoconazole is chemically known as (2S,4R)-cis-1-acetyl-4-[4-[[2-(2,4-dichlorophenyl)-2-(1H-imidazol-1-yl-methyl)-1,3-dioxolan-4-yl] methoxyl] phenyl] piperazine. Levoketoconazole has a molecular formula of $C_{26}H_{28}Cl_2N_4O_4$ with a molecular mass of 531.43 g/mol and may be depicted as shown below.

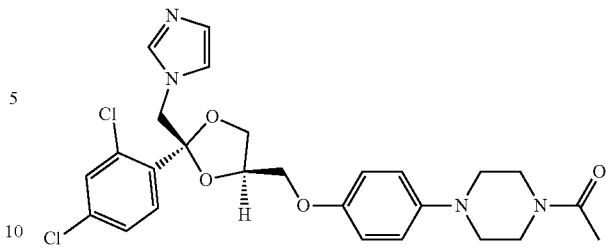

The (2S,4R)-enantiomer is active form of racemic ketoconazole and is a cortisol synthesis inhibitor. It is indicated for the treatment of endogenous hypercortisolemia in adult patients with Cushing's syndrome for whom surgery is not an option or has not been curative and it is not approved for the treatment of fungal infections.

Rotstein disclosed the preparation of four stereoisomers (2S,4R)-, (2R,4R)-, (2R,4S)-, and (2S,4S)- of ketoconazole using a multistep process for preparing ketoconazole stereoisomersstarting from 2', 4'-dichloroacetophenone.

Camps disclosed the preparation of (2S,4R)-enantiomer of ketoconazole from R-epichlorohydrin. This process involves around ten step process to obtain levoketoconazole, as shown in Scheme 1.

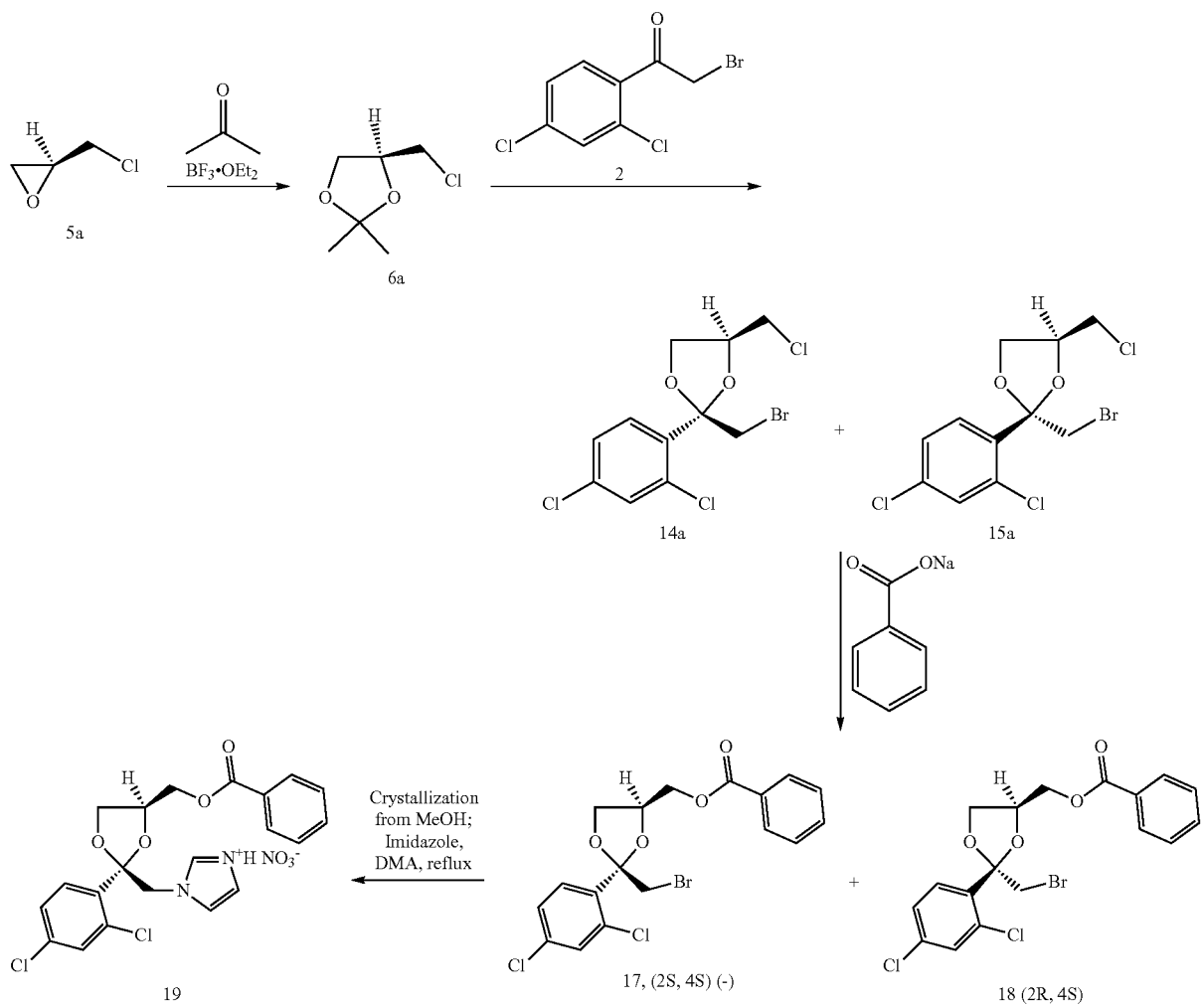

Scheme 1

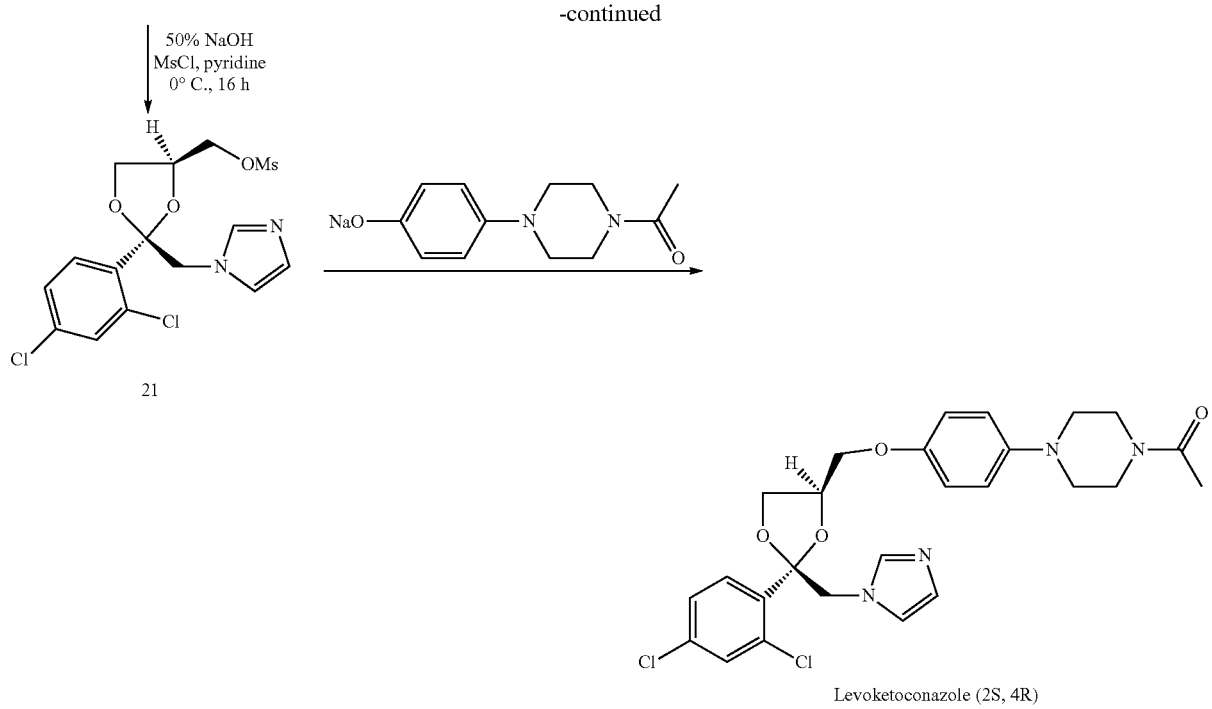

-continued

Levoketoconazole (2S, 4R)

The main disadvantage of prior processes is that these processes involve multistep and complex chemistry. Additionally, Camps' step-2 involves use of (S)-solketal-chloride (6a) resulting in a mixture that includes desired (14a) and undesired enantiomer (15a) as well as (±)-cis-2-(bromomethyl)-4-(chloromethyl)-2-(2,4-dichlorophenyl)-1,3-dioxolane, (+)-14a and (+)-15a which is further converted to desired compound 19 in subsequent following steps. In this process atleast 50% of unwanted material was removed during the preparation of 19 and there is 61% yield in the final step. The overall yield of the levoketoconazole obtained from this process is very low and it involves tedious step which are commercially not feasible and not suitable for commercial production.

Another disadvantage of the Rotstein and Camp methods is that the chemical purity may be unsuitable for use in humans and that the chiral purity of levoketoconazole obtained from prior process is about 99%, which is an unsatisfactory chiral purity that does not meet the regulatory requirements mandating higher chemical and chiral purity.

Gray and Marin reportedly disclose compositions including (2S,4R)-ketoconazole, but provide no details for the manufacture of said compositions.

There are other reported methods like chromatographic and HPLC methods for the separation of enantiomers of ketoconazole but these are industrially not viable.

Accordingly, there is a need for a commercially suitable process for preparing levoketoconazole which is industrially suitable for commercial production and having regulatory acceptable level of purity.

OBJECTIVE

An objective of the present disclosure is to provide a process for preparing levoketoconazole.

Another objective of the present disclosure is to provide a process for preparing levoketoconazole which is commercially suitable, and cost effective, and provides levoketoconazole that meets (or exceeds) regulatory requirements.

SUMMARY

Accordingly, the present disclosure relates to a process for preparing levoketoconazole, its salts, solvates, and solid-state forms thereof, comprising: a) providing racemic ketoconazole comprising (2S,4R)-cis-ketoconazole (levoketoconazole) and (2R,4S)-cis-ketoconazole (dextroketoconazole); b) contacting racemic ketoconazole with a resolution agent to obtain levoketoconazole; c) optionally purifying levoketoconazole; and d) isolating levoketoconazole.

The present disclosure also relates to a process for preparing levoketoconazole, its salts, solvates, and solid state-forms thereof comprising: a) providing racemic ketoconazole comprising (2S,4R)-cis-ketoconazole (levoketoconazole) and (2R,4S)-cis-ketoconazole (dextroketoconazole); b) deacylating racemic ketoconazole to obtain racemic desacetyl-ketoconazole comprising desacetyl-(2S,4R)-cis-ketoconazole (desacetyl-levoketoconazole) and desacetyl-(2R,4S)-cis-ketoconazole (desacetyl-dextroketoconazole); c) contacting racemic desacetyl-ketoconazole with a resolution agent to obtain desacetyl levoketoconazole; d) acylating desacetyl levoketoconazole to obtain levoketoconazole; e) optionally purifying levoketoconazole; and f) isolating levoketoconazole.

DETAILED DESCRIPTION OF DRAWINGS

FIG. 1. Powder X-ray diffraction pattern of crystalline levoketoconazole.

Figure 2:
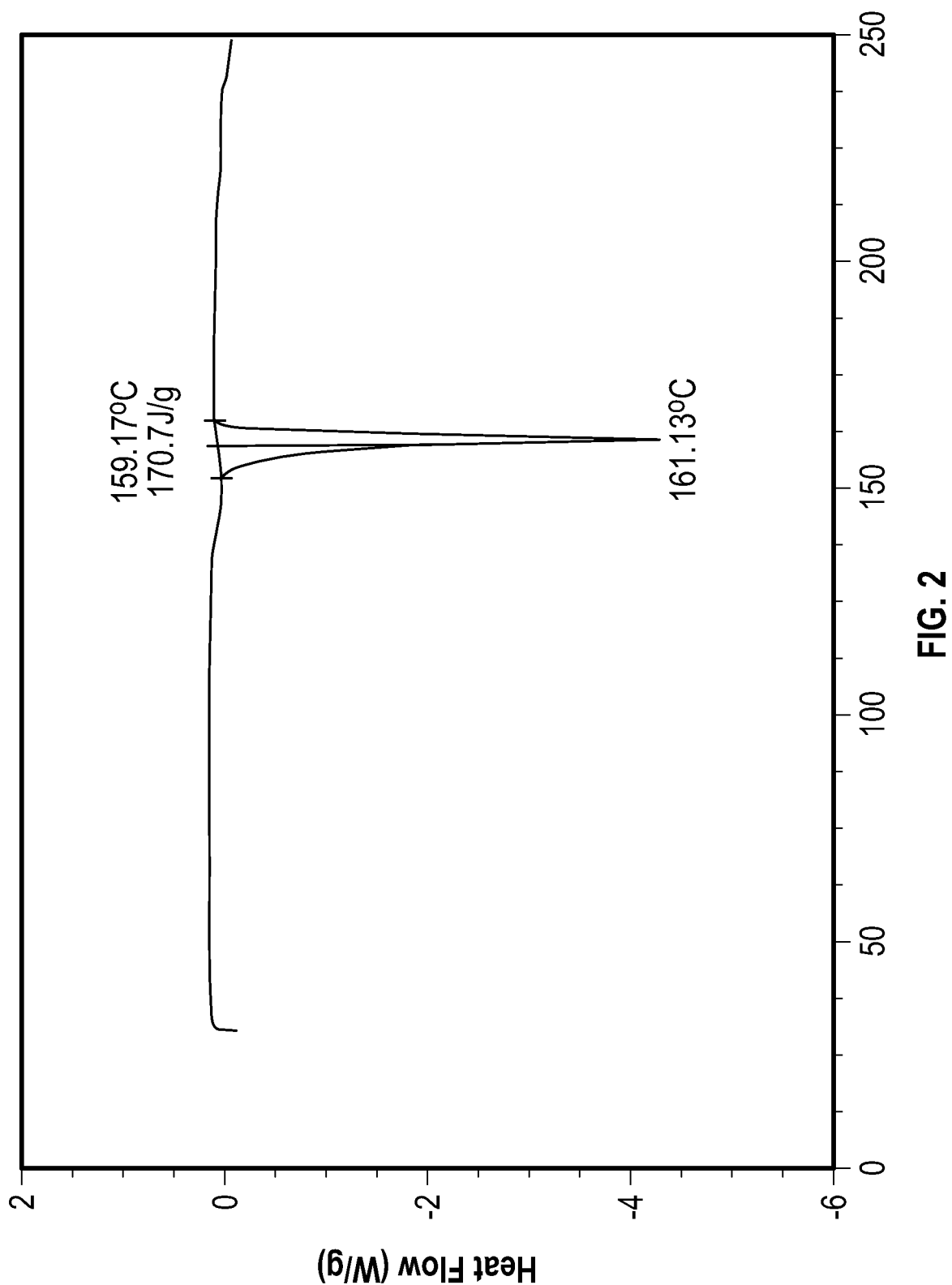

FIG. 2. Differential Scanning calorimetry (DSC) curve of crystalline levoketoconazole.

DETAILED DESCRIPTION

A first embodiment relates to a process for the preparing levoketoconazole, its salt, solvate (e.g., hydrate), and a solid-state form thereof, comprising: a) providing racemic ketoconazole comprising 2S,4R-cis-ketoconazole (levoketoconazole) and 2R,4S-cis-ketoconazole (dextroketoconazole); b) contacting racemic ketoconazole with a resolution agent to obtain levoketoconazole; c) optionally purifying levoketoconazole; and d) isolating levoketoconazole.

In one aspect of the first embodiment, step a) comprises dissolving racemic ketoconazole in a suitable solvent. Examples of suitable solvents include, but are not limited to, dichloromethane, dichloroethane, toluene, hexane, heptane, diethyl ether, diisopropyl ether, ethyl methyl ether, methyl tertiary-butyl ether, tetrahydrofuran, 2-methyl tetrahydrofuran, dioxane, N,N-dimethylformamide, N,N-dimethylacetamide, dimethyl sulfoxide, 1-methyl-2-pyrrolidone, 1-methyl-2-piperidone, 1,3-dimethyl-2-imidazolidinone, acetonitrile, acetone, pentanone methyl ethyl ketone, ethyl acetate, isopropyl acetate, methanol, ethanol, isopropanol, n-butanol, pentanol, octanol, water, or a combination thereof.

In yet another aspect of the first embodiment, step a) comprises dissolving racemic ketoconazole in a solvent comprising a polar aprotic solvent, a polar protic solvent, or a combination thereof. Examples of polar aprotic solvents, include, but are not limited to dichloromethane, dichloroethane, diethylether, diisopropyl ether, ethyl methyl ether, methyl tertiary-butyl ether, tetrahydrofuran, 2-methyl tetrahydrofuran, dioxane, NN-dimethylformamide, N,N-dimethylacetamide, dimethylsulfoxide, 1-methyl-2-pyrrolidone, 1-methyl-2-piperidone, 1,3-dimethyl-2-imidazolidinone, acetonitrile, acetone, pentanone methyl ethyl ketone, ethyl acetate, isopropyl acetate, or a combination thereof; while examples of polar protic solvents include, but are not limited to methanol, ethanol, isopropanol, n-butanol, pentanol, octanol, water, or a combination thereof.

In a further aspect of the first embodiment, step a) comprises dissolving racemic ketoconazole in a solvent comprising a polar aprotic solvent, a polar protic solvent, or a combination thereof, wherein the concentration of racemic ketoconazole in the solvent ranges from about 80 mg/mL to about 120 mg/mL and all values in between, including for example about 90 mg/mL, about 100 mg/mL, about 110 mg/mL.

In yet a further aspect of the first embodiment, step a) comprises dissolving racemic ketoconazole in a solvent comprising a polar aprotic solvent, a polar protic solvent, or a combination thereof, wherein the polar aprotic solvent ranges from about 90% v/v to about 100% v/v (e.g., about 90% v/v, about 91% v/v, about 92% v/v, about 93% v/v, about 94% v/v, about 95% v/v, about 96% v/v, about 97% v/v, about 98% v/v, and about 100% v/v) and the polar protic solvent ranges from about 0% v/v to about 10% v/v (e.g., about 0% v/v, about 1% v/v, about 2% v/v, about 3% v/v, about 4% v/v, about 5% v/v, about 6% v/v, about 7% v/v, about 8% v/v, about 9% v/v, and about 10% v/v).

In another aspect of the first embodiment, the resolution agent used in step b) is selected from (−)-dibenzoyl-L-tartaric acid monohydrate, (+)-dibenzoyl-D-tartaric acid monohydrate, (−)-di-p-toluoyl-L-tartaric acid, (+)-dibenzoyl-D-tartaric acid, D-(−)-tartaric acid, L-(+)-tartaric acid, dimethyl L-(+)-tartrate, dimethyl D-(−)-tartrate, diethyl L-(+)-tartrate, diethyl D-(−)-tartrate, diisopropyl L-(+)-tartrate, diisopropyl D-(−)-tartrate, (2R,3R)-tartranilic Acid, (S)-(+)-2-butanol, (R)-(−)-2-butanol, (S)-(−)-2-methyl-1-butanol, (S)-(+)-2-octanol, (R)-(−)-2-octanol, (R)-(+)-1-phenylethyl alcohol, (S)-(−)-1-phenylethyl alcohol, (R)-(−)-1-phenyl-2,2,2-trifluoroethanol, (S)-(+)-1-Phenyl-2,2,2-trifluoroethanol, (R)-(−)-1-(9-anthryl)-2,2,2-trifluoroethanol, (S)-(+)-1-(9-anthryl)-2,2,2-trifluoroethanol, (R)-(−)-1-amino-2-propanol, (S)-(+)-1-amino-2-propanol, (−)-cis-2-benzylamino-cyclohexane methanol, (+)-cis-2-benzylaminocyclohexanemethanol, (R,R)-(+)-bis(α-methylbenzyl) amine hydrochloride, (S,S)-(−)-bis(α-methylbenzyl)amine hydrochloride, (1R,2R)-1,2-bis(2-hydroxyphenyl)-ethylenediamine, (1S,2S)-1,2-bis(2-hydroxyphenyl)-ethylenediamine, (R)-(+)-1-(4-bromophenyl)-ethylamine, (S)-(−)-1-(4-bromophenyl)-ethylamine, (S)-(−)-N,N-dimethyl-1-phenylethylamine, (R)-(+)-N,N-dimethyl-1-phenylethylamine, (S)-1-(4-Nitrophenyl)ethylamine hydrochloride ((S)-nitresolve), (R)-1-(2-naphthyl)ethylamine, (5)-1-(2-naphthyl)ethylamine, (S)-(−)-1-phenylethylamine, (R)-(+)-1-phenylethylamine, brucine anhydrous, cinchonidine, cinchonine, quinine, quinidine, (+)-dehydroabietylamine, (R)-(−)-N-(3,5-dinitrobenzoyl)-60 -phenylethylamine, (R)-(+)-α- methylbenzylisocyanate, (S)-(−)-α-Methylbenzylisocyanate, (R)-(−)-1-(1-naphthyl)ethylisocyanate, (S)-(+)-1-(1-naphthyl)ethylisocyanate, (S)-(+)-α-methoxy-α- (trifluoromethyl)phenylacetyl chloride (MTPA-Cl), (R)-(−)-MTPA-Cl, (+)-menthyl chloroformate, (−)-menthyl chloroformate, methyl D-(−)-mandelate, methyl L-(+)-mandelate, (S)-(−)-N-(1-phenylethyl)-phthalamic Acid, (R)-(+)-N-(α-Methylbenzyl)-phthalamic Acid, (S)-(+)-α-methoxyphenylacetic acid, (R)-(−)-α-methoxyphenylacetic acid, (+)-MTPA, (−)-MTPA, (S)-(+)-γ-carboxy-γ-butyrolactone, (R)-(−)-γ-carboxy-γ-butyrolactone, (R)-(−)-hydratropic acid, (S)-(+)-hydratropic Acid, D-(+)-malic acid, L-(−)-malic acid, (−)-menthoxyacetic Acid, L-(+)-mandelic acid, D-(−)-mandelic acid, D-(−)-quinic acid, D-aspartic acid, L-aspartic acid, D-glutamic acid, L-glutamic acid, D-pyroglutamic acid, L-pyroglutamic acid, D-valine, L-valine, tosyl-L-phenylalanyl chloride, (+)-camphorsulfonic acid, (−)-camphorsulfonic acid, (+)-10-camphorsulfonyl chloride, (−)-10-camphorsulfonyl chloride, (−)-camphanic Acid, (−)-camphanic chloride, N-(2-Carboxybenzoyl)-(−)-10,2-camphorsultam, N-(2-carboxybenzoyl)-(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric Acid, (−)N-(2-carboxybenzoyl)-(−)-10,2-camphorsultam, N-(2-carboxybenzoyl)-(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric Acid, (1S,3R)-(−)-camphoric acid, (R)-(−)-1,1'-binaphthyl-2,2'-diyl hydrogen phosphate, (S)-(+)-1,1'-binaphthyl-2,2'-diyl hydrogen phosphate, (S)-5-allyl-2-oxabicyclo[3.3.0]oct-8-ene, (+)-MBF-OH dimer (CAS No. 87248-50-8), (−)-MBF-OH dimer (CAS No. 108031-79-4), or a combination thereof.

In another aspect, the mole ratio of racemic ketoconazole to resolution agent achieves suitable resolution of levoketoconazole and dextroketoconazole. In yet another aspect, the mole ratio of racemic ketoconazole to resolution agent ranges from about 0.80 to about 1.2 and all values in between, for example, about 0.85, about 0.90, about 0.95, about 1, about 1.05, about 1.1, and about 1.15.

In yet another aspect of the first embodiment, step a) comprises dissolving racemic ketoconazole in a solvent comprising a polar aprotic solvent, a polar protic solvent, or a combination thereof and step b) occurs at a temperature in the range of about 0° C. to a reflux temperature of solvent.

In yet another aspect of the first embodiment, step a) comprises dissolving racemic ketoconazole in a solvent comprising a polar aprotic solvent, a polar protic solvent, or a combination thereof, step b) occurs at a temperature in the range of about 0° C. to a reflux temperature of solvent.

In another aspect, step b) further comprises b1) contacting racemic ketoconazole with a resolution agent to obtain a levoketoconazole salt; and b2) contacting ketoconazole salt with base to obtain levoketoconazole.

In another aspect, the base for step b2) comprises an inorganic base, an organic base, or a combination thereof, wherein the base is selected from sodium hydroxide, potassium hydroxide, lithium hydroxide, sodium carbonate, potassium carbonate, lithium carbonate, sodium bicarbonate, potassium bicarbonate, lithium bicarbonate, trimethylamine, diisopropylamine, or a combination thereof.

In yet another aspect, step b) further comprises crystallizing levoketoconazole in the presence of the resolution agent and one or more solvents comprising a polar aprotic solvent, a polar protic solvent, or a combination thereof, wherein said crystallization comprises cooling the one or more solvents at a rate of about 0.1° C/min to about 10° C/min and all values in between, including, for example, about 0.2° C/min, about 0.4° C/min, about 0.6° C/min, about 0.8° C/min, about 1.0° C/min, about 2.0° C/min, about 4.0° C/min, about 6.0° C/min, and about 8.0° C/min.

In certain aspects, operation of steps a) and b) of the first embodiment results in levoketoconazole where the chemical and chiral purity of levoketoconazole may be suitable to produce a drug product used in a human. Thus, the optional step c) may be omitted and the levoketoconazole may be isolated. In certain aspects, it may be necessary to further purify levoketoconazole.

Accordingly, another aspect of the first embodiment further comprises step c) purifying levoketoconazole comprises crystallization of levoketoconazole in the presence of one or more solvents comprising a polar aprotic solvent, a polar protic solvent, or a combination thereof.

In another aspect, the purification is also carried out by contacting crude levoketoconazole with an acid such as anyone of resolution agents as disclosed herein to obtain pure enantiomeric excess amount of desired (2S,4R)-enantiomer.

Yet another aspect of the first embodiment relates to a process for the preparing levoketoconazole, its salt, solvate (e.g., hydrate), and a solid-state form thereof, comprising: a) dissolving racemic ketoconazole in a solvent comprising a polar aprotic solvent, a polar protic solvent, or a combination thereof; b1) contacting racemic ketoconazole with a resolution agent to obtain a salt comprising levoketoconazole and the resolution agent; b2) cooling the salt at a rate of about 0.1° C/min to about 10° C/min and all values in between; b3) isolating the salt; b4) contacting the salt with a base to obtain levoketoconazole; c) optionally purifying levoketoconazole; and d) isolating levoketoconazole.

Yet another aspect of the first embodiment relates to a process for the preparing levoketoconazole, its salt, solvate (e.g., hydrate), and a solid-state form thereof, comprising: a) dissolving racemic ketoconazole in a solvent comprising a polar aprotic solvent, a polar protic solvent, or a combination thereof; b1) contacting racemic ketoconazole with a resolution agent to obtain a salt comprising levoketoconazole and the resolution agent; b2) cooling the salt at a rate of about 0.1° C/min to about 10° C/min and all values in between; b3) isolating the salt; b4) contacting the salt with a base to obtain levoketoconazole; c) purifying levoketoconazole; and d) isolating levoketoconazole.

Yet another aspect of the first embodiment relates to a process for the preparing levoketoconazole, its salt, solvate (e.g., hydrate), and a solid-state form thereof, comprising: a) dissolving racemic ketoconazole in a solvent comprising a polar aprotic solvent, a polar protic solvent, or a combination thereof; b1) contacting racemic ketoconazole with a resolution agent to obtain a salt comprising levoketoconazole and the resolution agent; b2) cooling the salt at a rate of about 0.1° C/min to about 10° C/min and all values in between; b3) isolating the salt; b4) contacting the salt with a base to obtain levoketoconazole; c) purifying levoketoconazole by c1) dissolving levoketoconazole in an amount of methanol comprising from about 2 to about 6 volumes of methanol relative to the volume of levoketoconazole), c2) contacting the methanol solution from step c1) with a suitable amount of activated carbon (e.g., about 0.05 g to about 0.2 g per gram of levoketoconazole), c3) filtering the activated carbon from the methanol solution from step c2), c4) removing the methanol from step c3), and c5) crystallizing levoketoconazole from isopropanol (e.g., dissolving levoketoconazole obtained from step c4) in an amount of isopropanol comprising from about 4 to about 7 volumes of isopropanol relative to the volume of levoketoconazole, heating the levoketoconazole-isopropanol composition to an isopropanol reflux temperature (e.g., from 75° C. to about 83° C.), and cooling the levoketoconazole-isopropanol solution; and d) isolating levoketoconazole.

A second embodiment relates to a process for preparing levoketoconazole, its salts, solvates, and solid-state forms thereof comprising: a) providing racemic ketoconazole comprising (2S,4R)-cis-ketoconazole (levoketoconazole) and (2R,4S)-cis-ketoconazole (dextroketoconazole); b) deacylating racemic ketoconazole to obtain racemic desacetyl-ketoconazole comprising desacetyl-(2S,4R)-cis-ketoconazole (desacetyl-levoketoconazole) and desacetyl-(2R,4S)-cis-ketoconazole (desacetyl-dextroketoconazole); c) contacting racemic desacetyl-ketoconazole with a resolution agent to obtain desacetyl levoketoconazole; d) acylating desacetyl levoketoconazole to obtain levoketoconazole; e) optionally purifying levoketoconazole; and f) isolating levoketoconazole.

In an aspect of the second embodiment, step b) of deacylating racemic ketoconazole comprises contacting the racemic ketoconazole with a deacylating base comprising an inorganic base, an organic base, or a combination thereof, wherein the base is selected from sodium hydroxide, potassium hydroxide, lithium hydroxide, sodium carbonate, potassium carbonate, lithium carbonate, sodium bicarbonate, potassium bicarbonate, lithium bicarbonate, trimethylamine, triethylamine, N,N-diisopropylamine, or a combination thereof.

In yet another aspect, the mole ratio of racemic ketoconazole to deacylating base ranges from about 8.0 to about 12.5 and all values in between, for example, about 8.5, about 9.0, about 9.5, about 10.0, about 1.05, about 10.1, about 10.2, about 10.3, about 10.4, about 10.5, about 10.6, 10.7, about 10.8, about 10.9, about 11.0, about 11.1, 11.2, about 11.3, about 11.4, about 11.5, about 11.6, about 11.7, about 11.8, about 11.9, about 12.0, about 12.1, about 12.2, about 12.3, and about 12.4.

In an aspect of the second embodiment, step c) relates to the use of a resolution agent as disclosed herein.

In an aspect of the second embodiment, the acylation of step d) comprises use of a suitable acetylation reagent comprising acetyl chloride, acetic anhydride, or a combination thereof.

In an aspect of the second embodiment, purifying levoketoconazole occurs in one or more solvents in the presence (or absence) of a suitable acid and/or base.

In an aspect disclosed herein, the one more more solvents used for purification comprises water; an alcohol (e.g., methanol, ethanol, n-propanol, isopropanol, n-butanol, isobutanol, t-butanol, ethylene glycol, 1,2-propylene glycol, 2-methoxy ethanol, 1, 2-ethoxyethanol, diethylene glycol, 1-pentanol, 2-pentanol, or 3-pentanol, neo-pentyl alcohol, t-pentyl alcohol, diethylene glycol monoethyl ether, cyclohexanol, or glycerol, and a mixture thereof); a ketone (e.g., acetone, methyl ethyl ketone, methyl isobutyl ketone, and a mixture thereof); an ether (e.g., diethyl ether, tetrahydrofuran, 1,3-dioxane, 1,4-dioxane, dimethoxymethane, furan, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane, and a mixture thereof); a nitrile solvent (e.g., acetonitrile, propionitrile, isobutyronitrile, and a mixture thereof), an ester (e.g., methyl acetate, ethyl acetate, isopropyl acetate, n-butyl acetate, isobutyl acetate, and a mixture thereof); a hydrocarbon (e.g., n-hexane, n-heptane, cyclohexane, petroleum ether, benzene, toluene, pentane, cycloheptane, methyl cyclohexane, ethylbenzene, ortho, meta, or para-xylene, and a mixture thereof); a chloro solvent (e.g., dichloromethane, dichloroethane, chloroform, carbon tetrachloride, and a mixture thereof); a polar-aprotic solvent (e.g., dimethylacetamide (DMA), dimethylformamide (DMF), dimethylsulfoxide (DMSO), N-methylpyrrolidone (NMP), and a mixture thereof); or a combination thereof.

In another aspect, purifying levoketoconazole is carried out by using an acid which is selected from an organic acid, an inorganic acid, or a combination thereof including acids as disclosed herein.

In another embodiment of the present disclosure wherein the purification of levoketoconazole is carried out by using a base which is selected from an organic base, an inorganic base, or a combination thereof including bases as disclosed herein.

A third embodiment relates to crystalline levoketoconazole having a purity greater than 99.0% by HPLC.

Impurities include, but are not limited to, dextroketoconazole (CAS No. 142128-59-4), Impurity B (CAS No. 1346598-39-7 and its enantiomer), Impurity D (CAS No. 67914-61-8 and its enantiomer (CAS No. 133345-17-2)), Impurity E (CAS No. 134071-44-6 and its enantiomer), as well as the resolution agent, e.g., D-(+)-10-camphorsulphonic acid (CAS No. 3144-16-9).

In one aspect of the third embodiment the impurities listed above are removed by crystallization and purification of ketoconazole.

In another aspect of the third embodiment, the crystalline levoketoconazole comprises PXRD peaks at 17.4, 19.8 and 23.6±0.2 °2θ.

In another aspect, the crystalline levoketoconazole further comprises PXRD peaks at 10.4, 15.9, 18.7, 19.2, 20.3, 21.1 and 27.4±0.2°2θ.

In yet another aspect, the crystalline levoketoconazole has a PXRD pattern substantially as shown in FIG. 1.

And yet another aspect, the crystalline levoketoconazole has chiral purity about 99.5% by chiral HPLC.

In another aspect, the crystalline levoketoconazole has a chiral purity (by chiral HPLC) of about 99.55%, about 99.60%, about 99.65%, about 99.70%, about 99.75%, about 99.80%, about 99.85%, about 99.90%, about 99.95%, about 99.96%, about 99.97%, about 99.98%, about 99.99%, or about 100%.

In another aspect, the levoketoconazole obtained from present disclosure is crystalline having purity (by HPLC) greater than about 99.1%, about 99.2%, about 99.3%, about 99.4%, about 99.5%, about 99.6%, about 99.7%, about 99.8%, about 99.9%, about 99.98%.

In another aspect, the crystalline levoketoconazole has a purity greater than about 99.0% by HPLC and an individual impurity less than about 0.1% by HPLC.

In yet another aspect, the crystalline levoketoconazole has a purity greater than about 99.5% by HPLC and an individual impurity less than about 0.5% by HPLC.

In one aspect, the crystalline levoketoconazole has purity greater than about 99.5% by HPLC and an individual impurity less than about 0.09%, less than about 0.08%, less than about 0.07%, less than about 0.06%, less than about 0.05%, less than about 0.04%, less than about 0.03%, less than about 0.02%, less than about 0.01% or less than about 0.005% by HPLC.

In yet another aspect, the crystalline levoketoconazole has a DSC curve substantially as shown in FIG. 2.

In yet another aspect, the crystalline levoketoconazole has a DSC onset temperature of 159.2° C. Previously reported melting points for levoketoconazole include 155-157° C. (Rotstein, 2825) and 153-155 (Camps, 1294). Accordingly, the crystalline levoketoconazole disclosed herein exhibits a purity that substantially exceeds the levoketoconazole compositions of Rotstein and Camps.

Racemic ketoconazole for preparing levoketoconazole may be obtained by published methods. See, e.g., Heeres and Rotstein.

In another embodiment of the present disclosure wherein the purification of levoketoconazole is carried out by using a purification solvent, an acid, and a base.

An additional aspect relates to a crystalline salt comprising levoketoconazole and a resolution agent disclosed herein. For instance, additional aspects relate to a crystalline salt comprising levoketoconazole and any one of S-ibuprofen, dibenzoyl-L-tartaric acid, L-(+) tartaric acid, D-(+)-camphor sulfonic acid, and (R)-(−)-mandelic acid.

Another aspect relates to a crystalline salt comprising desacetyl-(2S,4R)-cis-ketoconazole and a resolution agent disclosed herein. For instance, additional aspects relate to a crystalline salt comprising desacetyl-(2S,4R)-cis-ketoconazole and any one of S-ibuprofen, dibenzoyl-L-tartaric acid, L-(+) tartaric acid, D-(+)-camphor sulfonic acid, and (R)-(−)-mandelic acid.

The levoketoconazole is poorly soluble in water and hence the lower particle size of levoketoconazole is advantageous to obtain a desired dissolution and bioavailability profile. Accordingly, one aspect of the present disclosure is the crystalline levoketoconazole particles have the desired particle size distribution, namely a particle size distribution in which: d90 is less than or equal to 100 μm, preferably less than or equal to 50 μm more preferably less than 30 μm; and $d_{50}$ is less than or equal to 30 μm, preferably less than or equal to 10 μm, more preferably less than 5 μm.

The crystalline levoketoconazole having reduced particle size obtained from the final crystallization process or by mechanical process including but not limited to milling or micronisation.

The flowability of crystalline levoketoconazole may be characterized by the Hausner Ratio and/or the Carr's compressibility index (also known as the Compressibility Index). See Wells and USP <1174>.

The Hausner Ratio is a value calculated by dividing the tapped density of the levoketoconazole by the freely settled bulk density of the levoketoconazole. The freely settled bulk density is calculated by pouring a known weight of material into a measuring cylinder and recording the volume. The tapped density is calculated by tapping the cylinder against a surface for a specified numbers of times and recording again the new volume. The following table shows the terms used to describe the flowability character with reference to the Hausner Ratio and Compressibility Index.

| Flow Character | Hausner Ratio | Compressibility Index (%) |
|---|---|---|
| Excellent | 1.00-1.11 | ≤10 |
| Good | 1.12-1.18 | 11-15 |
| Fair | 1.19-1.25 | 16-20 |
| Passable | 1.26-1.34 | 21-25 |
| Poor | 1.35-1.45 | 26-31 |
| Very Poor | 1.46-1.59 | 32-37 |
| Very, very poor | >1.60 | >38 |

The Hausner Ratio for crystalline levoketoconazole disclosed herein was determined in a manner consistent with the USP recommended procedure (see USP <1174>, including, e.g., 100 g sample a 250 mL graduated cylinder with a height of about 31 cm and a diameter of about 4.5 cm, including tap numbers of 500 and 1250. Based on experimental findings, crystalline levoketoconazole disclosed herein has a bulk density of about 0.576 g/mL and a tapped density after 500 taps of about 0.686 g/mL and a tapped density after 1,250 taps of about 0.681 g/mL. Thus, the Hausner Ratio of the crystalline levoketoconazole for 500 taps is 1.120 and for 1250 taps is 1.18 which shows that crystalline levoketoconazole disclosed herein has good flowability.

The Carr (or Compressibility) Index is frequently used in pharmaceutics as an indication of the compressibility of a powder. The Carr Index may be calculated by dividing the difference of the tapped and bulk densities by the tapped density and then multiplying by 100. In a free-flowing powder, the bulk density and tapped density would be close in value; therefore, the Carr Index would be small. On the other hand, in a poor-flowing powder where there are greater interparticle interactions, the difference between the bulk and tapped density observed would be greater, therefore, the Carr Index would be larger. A Carr Index greater than 25 is considered to be an indication of poor flowability and below 15, of good flowability and the Carr Index of the crystalline levoketoconazole of the present disclosure is less than 15.

The present disclosure is provided by the examples below, which are provided by 15 way of illustration only and should not be considered to limit the scope of the subject matter claimed herein.

Examples

HPLC parameters for Data detection

| | |
|---|---|
| Column details | Thermo scientific (Hypersil BDS C18) Dimensions (100 mm × 4.6 mm), ID 3.0 μm |
| Column temperature | 25° C. |
| Sample temperature | 5° C. |
| Flow rate | 2.0 mL/min |
| Wavelength | 225 nm |
| Injection volume | 10 μL |
| Run time | 30 minutes |
| Retention time of Levo ketoconazole | About 8.0 minutes |
| Needle wash solution | 100% Methanol |
| Column washing solution | Water: Methanol (80:20) v/v, and followed by Methanol: Water: (80:20) v/v |

Chiral HPLC Parameters

| | |
|---|---|
| Column details | Chiral PAK AD-H; 250 mm × 4.6 mm ID, 5.0 μm |
| Column oven temperature | 35° C. |
| Sample temperature | 10° C. |

-continued

Examples

| | |
|---|---|
| Flow rate | 1.0 mL/min (Isocratic) |
| Wavelength | 225 nm |
| Retention time Dextroketoconazole | ≈12.6 minutes |
| Retention time Levoketoconazole | ≈20.4 minutes |
| Injection volume | 10 μL |
| Run time | 35 minutes |
| Needle wash solution | Ethanol |
| Column washing solution | Hexane (70% v/v): IPA (30% v/v) |

PXRD parameters for Data detection

| | |
|---|---|
| Instrument | PANalytical |
| Scan Axis | Gonio |
| Start Position | [°2θ] 2.5197 |
| End Position | [°2θ] 49.9827 |
| Step Size | [°2θ] 0.0390 |
| Scan Step Time [s] | 164.9850 |
| Scan Type | Continuous |
| PSD Mode | Scanning |
| PSD Length [°2θ] | 3.35 |
| Offset [°2θ] | 0.0000 |
| Divergence Slit Type | Fixed |
| Divergence Slit Size [°] | 0.3599 |
| Specimen Length [mm] | 10.00 |
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 30 mA, 45 kV |
| Diffractometer Number | 0 |
| Goniometer Radius [mm] | 240.00 |
| Dist. Focus-Diverg. Slit [mm] | 60.50 |
| Incident Beam Monochromator | No |
| Spinning | No |

Differential Scanning Calorimetry (DSC) Method:
Levoketoconazole samples were analyzed by filling the respective levoketoconazole sample in the closed pan and other instrumental parameters were given below
  Instrument Make & Model TA instruments & Q20
  Software Thermal Advantage Release 5.4.0.
  Initial temperature 30° C.
  Final temperature 250° C.
  Ramp 10° C/minute
  Nitrogen flow 50 mL/minute
  Sample weight 3-5 mg Example 1: Preparation of Salt of Levoketoconazole and D-(+)-Camphor Sulfonic Acid To a 50 g of ketoconazole (94.1 mmol) 500 mL of acetone was added and stirred, 25 g of D-(+) camphor sulfonic acid (107.6 mmol) was added and the reaction mass was heated to reflux temperature. To the reaction mass 10 mL of water was added at same temperature. The reaction mass was cooled to room temperature and stirred. The obtained solid was filtered and washed with acetone and dried.

Example 2: Preparation of Salt of Levoketoconazole and L-(+) tartaric Acid

To a 50 g of ketoconazole 500 mL of isopropanol was added and stirred, L-(+) tartaric acid (1 eq.) was added and the reaction mass was heated to reflux temperature. To the reaction mass 250 mL of dioxane was added and stirred for 6 hours. The reaction mass was cooled to room temperature and stirred. The reaction mass was cooled to room temperature and stirred. The obtained solid was filtered and washed with isopropanol and dried.

Example 3: Preparation of Salt of Levoketoconazole and Dibenzoyl-L-Tartaric Acid To a 50 g of ketoconazole 500 mL of isopropanol was added and stirred, dibenzoyl-L-tartaric acid monohydrate (1 eq.) was added and the reaction mass was heated to reflux temperature under stirring and continued at same temperature for 5 hours. The reaction mass was cooled to room temperature and stirred. The obtained solid was filtered and washed with methanol and dried.

Example 4: Preparation of Salt of Levoketoconazole and S-Ibuprofen

To a 50 g of ketoconazole 500 mL of isopropanol was added and stirred, S-ibuprofen (1 eq.) was added and the reaction mass was heated to get the clear solution. The reaction mass was cooled to room temperature and stirred. The obtained solid was filtered and washed with methanol and dried.

Example 5: Preparation of Levoketoconazole

To a 950 mL of acetonitrile 100 g of ketoconazole (188.2 mmol) and 43.52 g of D-(+)-camphor sulphonic acid (187.3 mmol) were added at room temperature. The reaction mass was stirred at 25-35° C. for 10 mins, heated to 75-80° C. and stirred for 30-40 minutes. To the reaction mass 10 mL of water was added at 75-80° C. and gradually cooled to room temperature, stirred for 12 hours and filtered. The reaction mass was washed with mixture of acetonitrile and water, sucked dried and dried under vacuum.

The obtained product was added to 250 mL of dichloromethane and 250 mL of water was added. The pH of the reaction mass was adjusted to 7.5 to 8.5 with sodium bicarbonate solution and stirred for 30 minutes. The layers were settled, and the organic layer was separated. The aqueous layer was extracted with dichloromethane and the organic layer was separated. The combined organic layer was extracted with water and layers were separated. The organic layer was treated with activated carbon, filtered through celite bed, bed was washed with dichloromethane and the filtrate was distilled under vacuum at 40-45° C. To the residue 2 volume of methanol with respect to the residue was added and distilled. To the residue 4 volume of methanol with respect to the residue was added with respect to (w.r.t) the residue was added, heated the mass to 60-65° C. to get the clear solution and stirred for 30-40 minutes. The reaction mass was treated with carbon, stirred, and filtered through celite bed then distilled under vacuum at 60-65° C. To the residue isopropanol (5V w.r.t. to residue) was added at 50-55° C., reaction mass was heated to 75-80° C. and added excess isopropanol till clear solution was obtained 75-80° C. and stirred for 6-7 hours. The obtained solid was filtered, washed with IPA, sucked dried and dried under vacuum to obtain crystalline levoketoconazole, as shown in FIG. 1, having a chemical purity of >99.95% (by HPLC) and a chiral purity 99.99% (by chiral HPLC). The DSC curve (FIG. 2) shows an onset temperature of 159.17° C. and a peak of 161.13° C.

Example 6: Preparation of levoketoconazole a) Preparation of racemic desacetyl-ketoconazole To a 250 g of racemic ketoconazole (470.4 mmol), 3.75 L of methanol was added and stirred, to the reaction mass 213 g of sodium hydroxide 4.26 L was added at room temperature. The reaction mass was heated to 50-55° C. and maintained for 18 to 24 hours. After completion of the reaction, the reaction mass was cooled to 20° C. and washed with water. The solid was filtered and obtained solid was washed with water. The solid was recrystallized with methanol to obtain pure racemic desacetyl-levoketoconazole.

Any one of the resolution agents disclosed herein (e.g., Examples 1-4) may be used to obtain an enriched enantiomer of desacetyl-levoketoconazole. Alternatively, resolution of racemic desacetyl-ketoconazole may be achieved as follows.

b) Resolution of racemic desacetyl-ketoconazole

To a 20 g of racemic desacetyl-ketoconazole (4.0 mmol), 200 mL of acetone was added and stirred. To the reaction mass 6.5 g of (R)-(−)-mandelic acid (4.3 mmol) was added and the reaction mass was heated to reflux temperature. To the reaction mass, 300 mL of water was added and stirred for 2 hours. After completion of the reaction the reaction mass was cooled to room temperature and stirred. The obtained solid was washed with acetone and dried. The obtained solid was heated to reflux temperature with acetone and hot methanol was added to the reaction mass and stirred a reflux temperature for 30 minutes. The reaction mass was cooled to room temperature and stirred. The obtained solid was filtered and washed with acetone to obtain pure desacetyl levoketoconazole.

c) Acetylation of desacetyl levoketoconazole:

To a 10 g of desacetyl levoketoconazole (20.4 mmol), 100 mL of dichloromethane was added and the reaction was cooled to 25-35° C. The pH of the reaction mass was adjusted with 12-14 using 20% sodium hydroxide solution. The layers were separated, and the organic layer was washed with water and dried with sodium sulphate. To the organic layer 2.4 mL of triethylamine (17.2 mmol) and 2.23 mL of acetic anhydride (23.6 mmol) was added and stirred for 6 hours. After completion of the reaction, the reaction mass was extracted with brine solution and dried with sodium sulphate. The obtained solid was filtered and dried to yield levoketoconazole 96.7% enantiomer. This crude material was further enriched by method as disclosed herein (e.g., as in Example 5) to obtain >99.5% of levoketoconazole by HPLC.

CITED INFORMATION

Camps et al., *Stereoselective Syntheses of Both Enantiomers of Ketoconazole from(R)- and (S)-Epichlorohydrin*, Tetrahedron: Asymmetry (1995) 6(6): 1283-1294, 1995 ("Camps").

Heeres et al., *Antimycotic Imidazoles. Part 4. Synthesis and Antifungal Activity of Ketoconazole, a New Potent Orally Active Broad-Spectrum Antifungal Agent*, J. Med. Chem. (1979) 22(8): 1003-1005 ("Heeres").

International Patent Application No. WO 2006/072881 A1, *Methods and compositions for treating diabetes, metabolic syndrome and other conditions*, published on Jul. 13, 2006, to Per Märin of Cortendo AB ("Marin").

Rotstein et al., *Stereoisomers of Ketoconazole: Preparation and Biological Activity*' J. Med. Chem, 1992(35): 2818-2825 ("Rotstein").

U.S. Pat. No. 6,040,307, *Methods and compositions of (−)-ketoconazole for treating fungal yeast and dermatophyte infections*, issued on Mar. 21, 2000, to Gray et al. of Sepracor, Inc. ("Gray").

United States Pharmacopoeia, Chapter <1174>Powder Flow (2012) ("USP <1174>").

Wells, J. Chapter 8 (pp. 133-134) in Pharmaceutics: The Science of Dosage Form Design (M. E. Aulton ed., $2^{nd}$ Ed. 2002) ("Wells").

The invention claimed is:

1. A process for preparing levoketoconazole and its salts or solid-state forms thereof comprising:
   a) providing racemic ketoconazole;
   b) contacting racemic ketoconazole with a resolution agent to obtain levoketoconazole;
   c) optionally purifying levoketoconazole; and
   d) isolating levoketoconazole.

2. The process of claim 1, wherein providing racemic ketoconazole comprises dissolving racemic ketoconazole in a first solvent comprising dichloromethane, dichloroethane, toluene, hexane, heptane, diethylether, diisopropyl ether, ethyl methyl ether, methyltertiarybutyl ether, tetrahydrofuran, 2-methyl tetrahydrofuran, dioxane, N, N-dimethylformamide, N, N-dimethylacetamide, dimethylsulfoxide, 1-methyl-2-pyrrolidone, 1-methyl-2-piperidone, 1,3-dimethyl-2-imidazolidinone, acetonitrile, acetone, pentanone methyl ethyl ketone, ethyl acetate, isopropyl acetate, methanol, ethanol, isopropanol, n-butanol, pentanol, octanol, water, or a combination thereof.

3. The process of claim 1, wherein the resolution agent used in step b) comprises (−)-dibenzoyl-L-tartaric acid monohydrate, (+)-dibenzoyl-D-tartaric acid monohydrate, (−)-di-p-toluoyl-L-tartaric acid, (+)-dibenzoyl-D-tartaric acid, D-(−)-tartaric acid, L-(+)-tartaric acid, dimethyl L-(+)-tartrate, dimethyl D-(−)-tartrate, diethyl L-(+)-tartrate, diethyl D-(−)-tartrate, diisopropyl L-(+)-tartrate, diisopropyl D-(−)-tartrate, (2R,3R)-tartranilic Acid, (S)-(+)-2-butanol, (R)-(−)-2-butanol, (S)-(−)-2 -methyl-1-butanol, (S)-(+)-2-octanol, (R)-(−)-2-octanol, (R)-(+)-1-phenylethyl alcohol, (S)-(−)-1-phenylethyl alcohol, (R)-(−)-1-phenyl-2,2,2-trifluoroethanol, (S)-(+)-1-Phenyl-2,2,2-trifluoroethanol, (R)-(−)-1-(9-anthryl)-2,2,2-trifluoroethanol, (S)-(+)-1-(9-anthryl)-2,2,2-trifluoroethanol, (R)-(−)-1-amino-2-propanol, (S)-(+)-1-amino-2-propanol, (−)-cis-2-benzylaminocyclohexanemethanol, (+)-cis-2-benzylamino-cyclohexanemethanol, (R,R)-(+)-bis(α-methylbenzyl)amine hydrochloride, (S,S)-(−)-bis(α-methylbenzyl)amine hydrochloride, (1R,2R)-1,2-bis(2-hydroxyphenyl)-ethylenediamine, (1S,2S)-1,2-bis(2-hydroxyphenyl)-ethylenediamine, (R)-(+)-1-(4-bromophenyl)-ethylamine, (S)-(−)-1-(4-bromophenyl)-ethylamine, (S)-(−)-N,N-dimethyl-1-phenylethylamine, (R)-(+)-N,N-dimethyl-1-phenylethylamine, (S)-1-(4-Nitrophenyl)ethylamine hydrochloride ((S)-nitresolve), (R)-1-(2-naphthyl)ethylamine, (S)-1-(2-naphthyl)ethylamine, (S)-(−)-1-phenylethylamine, (R)-(+)-1-phenylethylamine, brucine anhydrous, cinchonidine, cinchonine, quinine, quinidine, (+)-dehydroabietylamine, (R)-(−)-N-(3,5-dinitrob enzoyl)-α-phenylethylamine, (R)-(+)-α-methylbenzyli socyanate, (S)-(−)-α-Methylbenzyli socyanate, (R)-(−)-1-(1-naphthyl)ethyli socyanate, (S)-(+)-1-(1-naphthyl)ethyli socyanate, (S)-(+)-α-methoxy-α-(trifluoromethyl)phenylacetyl chloride (MTPA-Cl), (R)-(−)-MTPA-Cl, (+)-menthyl chloroformate, (−)-menthyl chloroformate, methyl D-(−)-mandelate, methyl L-(+)-mandelate, (S)-(−)-N-(1-phenylethyl)-phthalamic Acid, (R)-(+)-N-(α-Methylbenzyl)-phthalamic Acid, (S)-(+)-α-methoxyphenylacetic acid, (R)-(−)-α-methoxyphenylacetic acid, (+)-MTPA, (−)-MTPA, (S)-(+)-γ-carboxy-γ-butyrolactone, (R)-(−)-γ-carboxy-γ-butyrolactone, (R)-(−)-hydratropic acid, (S)-(+)-hydratropic Acid, d-(+)-malic acid, 1-(−)-malic acid, (−)-menthoxyacetic Acid, L-(−)-mandelic acid, D-(−)-mandelic acid, D-(−)-quinic acid, D-aspartic acid, L-aspartic acid, D-glutamic acid, L-glutamic acid, D-pyroglutamic acid, L-pyroglutamic acid, D-valine, L-valine, tosyl-L-phenylalanyl chloride, (+)-camphorsulfonic acid, (−)-camphorsulfonic acid, (+)-10-camphorsulfonyl chloride, (−)-10-camphorsulfonyl chloride, (−)-camphanic acid, (−)-camphanic chloride, N-(2-Carboxybenzoyl)-(−)-10,2-camphorsultam, N-(2-carboxybenzoyl)-(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric Acid, (−)-camphanic chloride, N-(2-carboxybenzoyl)-(−)-10,2-camphorsultam, N-(2-carboxybenzoyl)-(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric Acid, (1S,3R)-(−)-camphoric acid, (R)-(−)-1,1'-binaphthyl-2,2'-diyl hydrogen phosphate, (S)-(+)-1,1'-binaphthyl-2,2'-diyl hydrogen phosphate, (S)-5-allyl-2-oxabicyclo[3.3.0] oct-8-ene, (+)-MBF-OH dimer, (−)-MBF-OH dimer, or a combination thereof.

4. The process of claim 1 wherein step b) occurs in a solvent at a temperature in the range of about 0° C. to a reflux temperature of the solvent.

5. The process of claim 1, wherein step b) further comprises
b1. contacting racemic ketoconazole with a resolution agent to obtain a levoketoconazole salt; and
b2. contacting the levoketoconazole salt with base to obtain levoketoconazole.

6. The process of claim 5, wherein the resolution agent comprises (−)-dibenzoyl-L-tartaric acid monohydrate, (+)-dibenzoyl-D-tartaric acid monohydrate, (−)-di-p-toluoyl-L-tartaric acid, (+)-dibenzoyl-D-tartaric acid, D-(−)-tartaric acid, L-(+)-tartaric acid, dimethyl L-(+)-tartrate, dimethyl D-(−)-tartrate, diethyl L-(+)-tartrate, diethyl D-(−)-tartrate, diisopropyl L-(+)-tartrate, diisopropyl D-(−)-tartrate, 2R,3R)-tartranilic Acid, (S)-(+)-2-butanol, (R)-(−)-2-butanol, (S)-(−)-2-methyl-1-butanol, (S)-(+)-2-octanol, (R)-(−)-2-octanol, (R)-(+)-1-phenylethyl alcohol, (S)-(−)-1-phenylethyl alcohol, (R)-(−)-1-phenyl- 2,2,2-trifluoroethanol, (S)-(+)-1-Phenyl-2,2,2-trifluoroethanol, (R)-(−)-1-(9-anthryl)-2,2,2-trifluoroethanol, (S)-(+)-1-(9-anthryl)-2,2,2-trifluoroethanol, (R)-(−)-1-amino-2-propanol, (S)-(+)-1-amino-2-propanol, (−)-cis-2-benzylaminocyclohexanemethanol, (+)-cis-2-benzylaminocyclohexanemethanol, (R,R)-(+)-bis(α-methylbenzyl)amine hydrochloride, (S,S)-(−)-bis(α-methylbenzyl)amine hydrochloride, (1R,2R)-1,2-bis(2-hydroxyphenyl)-ethylenediamine, (1S,2S)-1,2-bis(2-hydroxyphenyl)-ethylenediamine, (R)-(+)-1-(4-bromophenyl)-ethylamine, (S)-(−)-1-(4-bromophenyl)-ethylamine, (S)-(−)-N,N-dimethyl-1-phenylethylamine, (R)-(+)-N,N-dimethyl-1-phenylethylamine, (S)-1-(4-Nitrophenyl)ethylamine hydrochloride ((S)-nitresolve), (R)-1-(2-naphthyl)ethylamine, (S)-1-(2-naphthyl)ethylamine, (S)-(−)-1-phenylethylamine, (R)-(+)-1-phenylethylamine, brucine anhydrous, cinchonidine, cinchonine, quinine, quinidine, (+)-dehydroabietylamine, (R)-(−)-N-(3,5-dinitrobenzoyl)-α-phenylethylamine, (R)-(+)-α-methylbenzylisocyanate, (S)-(−)-α-Methylbenzyli socyanate, (R)-(−)-1-(1-naphthyl) ethylisocyanate, (S)-(+)-1-(1-naphthyl)ethylisocyanate, (S)-(+)-α-methoxy-α-(trifluoromethyl)phenylacetyl chloride (MTPA-Cl), (R)-(−)-MTPA-Cl, (+)-menthyl chloroformate, (−)-menthyl chloroformate, methyl D-(−)-mandelate, methyl L-(+)-mandelate, (S)-(−)-N-(1-phenylethyl)-phthalamic Acid, (R)-(+)-N-(a-Methylbenzyl)-phthalamic Acid, (S)-(+)-α-methoxyphenylacetic acid, (R)-(−)-α-methoxyphenylacetic acid, (+)-MTPA, (−)-MTPA, (S)-(+)-γ-carboxy-γ-butyrolactone, (R)-(—)-γ-carboxy-γ-butyrolactone, (R)-(−)-hydratropic acid, (S)-(+)-hydratropic Acid, D-(+)-malic acid, L-(−)-malic acid, (−)-menthoxyacetic Acid, L-(+)-mandelic acid, D-(−)-mandelic acid, D-(−)-quinic acid, D-aspartic acid, L-aspartic acid, D-glutamic acid, L-glutamic acid, D-pyroglutamic acid, L-pyroglutamic acid, D-valine, L-valine, tosyl-L-phenylalanyl chloride, (+)-camphorsulfonic acid, (−)-camphorsulfonic acid, (+)-10-camphorsulfonyl chloride, (−) -10-camphorsulfonyl chloride, (−)-camphanic acid, (−)-camphanic chloride, N-(2-Carboxybenzoyl)-(−)-10,2-camphorsultam, N-(2-carboxybenzoyl)-

(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric Acid, (−)-camphanic chloride, N-(2-carboxybenzoyl)-(−)-10,2-camphorsultam, N-(2-carboxybenzoyl)-(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric Acid, (1S,3R)-(−)-camphoric acid, (R)-(−)-1,1'-binaphthyl-2,2'-diyl hydrogen phosphate, (S)-(+)-1,1'-binaphthyl-2,2'-diyl hydrogen phosphate, (S)-5-allyl-2-oxabicyclo[3.3.0]oct-8-ene, (+)-MBF-OH dimer, (−)-MBF-OH dimer, or a combination thereof.

7. The process of claim 5, wherein the base comprises an inorganic base, an organic base, or a combination thereof and wherein the base comprises sodium hydroxide, potassium hydroxide, lithium hydroxide, sodium carbonate, potassium carbonate, lithium carbonate, sodium bicarbonate, potassium bicarbonate, lithium bicarbonate, trimethylamine, diisopropylamine, or a combination thereof.

8. The process of claim 1, comprising step c) purifying levoketoconazole.

9. The process of claim 8, wherein the purifying levoketoconazole comprises contacting the product of the resolution agent and the levoketoconazole with one or more a purification solvent, an acid, and a base.

10. The process of claim 9, wherein the purification solvent comprises water, an alcohol, a ketone, an ether, a nitrile solvent, an ester, a hydrocarbon, a chloro solvent, a polar-aprotic solvent, or a combination thereof.

11. A process for preparing levoketoconazole, its salt, solvate, or solid-state form thereof comprising:
   a) providing racemic ketoconazole in a solvent;
   b) deacylating racemic ketoconazole to obtain racemic desacetyl-ketoconazole;
   c) contacting racemic desacetyl-ketoconazole with a resolution agent to obtain desacetyl-(2S,4R)-cis-ketoconazole;
   d) acetylating desacetyl-(2S,4R)-cis-ketoconazole to obtain levoketoconazole;
   e) optionally purifying levoketoconazole; and
   f) isolating levoketoconazole.

12. The process of claim 11, wherein the solvent comprises dichloromethane, dichloroethane, toluene, hexane, heptane, diethylether, diisopropyl ether, ethyl methyl ether, methyltertiarybutyl ether, tetrahydrofuran, 2-methyl tetrahydrofuran, dioxane, N, N-dimethylformamide, N, N-dimethylacetamide, dimethylsulfoxide, 1-methyl-2-pyrrolidone, 1-methyl-2-piperidone, 1,3-dimethyl-2-imidazolidinone, acetonitrile, acetone, pentanone methyl ethyl ketone, ethyl acetate, isopropyl acetate, methanol, ethanol, isopropanol, n-butanol, pentanol, octanol, water, or a combination thereof.

13. The process of claim 11, wherein step b) comprises contacting the racemic ketoconazole with a deacylating base comprising an inorganic base, an organic base, or a combination thereof, wherein the deacylating base comprises sodium hydroxide, potassium hydroxide, lithium hydroxide, sodium carbonate, potassium carbonate, lithium carbonate, sodium bicarbonate, potassium bicarbonate, lithium bicarbonate, trimethylamine, diisopropylamine, or a combination thereof.

14. The process of claim 11, wherein the resolution agent comprises (−)-dibenzoyl-L-tartaric acid monohydrate, (+)-dibenzoyl-D-tartaric acid monohydrate, (−)-di-p-toluoyl-L-tartaric acid, (+)-dibenzoyl-D-tartaric acid, D-(−)-tartaric acid, L-(+)-tartaric acid, dimethyl L-(+)-tartrate, dimethyl D-(−)-tartrate, diethyl L-(+)-tartrate, diethyl D-(−)-tartrate, diisopropyl L-(+)-tartrate, diisopropyl D-(−)-tartrate, (2R, 3R)-tartranilic Acid, (S)-(+)-2-butanol, (R)-(−)-2-butanol, (S)-(−)-2-methyl-1-butanol, (S)-(+)-2-octanol, (R)-(−)-2-octanol, (R)-(+)-1-phenylethyl alcohol, (S)-(−)-1-phenylethyl alcohol, (R)-(−)-1-phenyl-2,2,2-trifluoroethanol, (S)-(+)-1-Phenyl-2,2,2-trifluoroethanol, (R)-(−)-1-(9-anthryl)-2,2,2-trifluoroethanol, (S)-(+)-1-(9-anthryl)-2,2,2-trifluoroethanol, (R)-(−)-1-amino-2-propanol, (S)-(+)-1-amino-2-propanol, (−)-cis-2-benzylaminocyclohexanemethanol, (+)-cis-2-benzylamino-cyclohexanemethanol, (R,R)-(+)-bis(α-methylbenzyl)amine hydrochloride, (S,S)-(−)-bis(α-methylbenzyl)amine hydrochloride, (1R,2R)-1,2-bis(2-hydroxyphenyl)-ethylenediamine, (1S,2S)-1,2-bis(2-hydroxyphenyl)-ethylenediamine, (R)-(+)-1-(4-bromophenyl)-ethylamine, (S)-(−)-1-(4-bromophenyl)-ethylamine, (S)-(−)-N,N-dimethyl-1-phenylethylamine, (R)-(+)-N,N-dimethyl-1-phenylethylamine, (S)-1-(4-Nitrophenyl)ethylamine hydrochloride ((S)-nitresolve), (R)-1-(2-naphthyl)ethylamine,(S)-1-(2-naphthyl)ethylamine, (S)-(−)-1-phenylethylamine, (R)-(+)-1-phenylethylamine, brucine anhydrous, cinchonidine, cinchonine, quinine, quinidine, (+)-dehydroabietylamine, (R)-(−)-N-(3,5-dinitrobenzoyl)-α-phenylethylamine, (R)-(+)-α-methylbenzylisocyanate, (S)-(−)-α-Methylbenzylisocyanate, (R)-(−)-1-(1-naphthyl)ethylisocyanate, (S)-(+)-1-(1-naphthyl)ethylisocyanate, (S)-(+)-α-methoxy-α-(trifluoromethyl)phenylacetyl chloride (MTPA-Cl), (R)-(−)-MTPA-Cl, (+)-menthyl chloroformate, (−)-menthyl chloroformate, methyl D-(−)-mandelate, methyl L-(+)-mandelate, (S)-(−)-N-(1-phenylethyl)-phthalamic Acid, (R)-(+)-N-(α-Methylbenzyl)-phthalamic Acid, (S)-(+)-α-methoxyphenylacetic acid, (R)-(−)-α-methoxyphenylacetic acid, (+)-MTPA, (−)-MTPA, (S)-(+)(γ-carboxy-γ-butyrolactone, (R)-(−)-γ-carboxy-γ-butyrolactone, (R)-(−)-hydratropic acid, (S)-(+)-hydratropic acid, D-(+)-malic acid, L-(−)-malic acid, (−)-menthoxyacetic acid, L-(+)-mandelic acid, D-(−)-mandelic acid, D-(−)-quinic acid, D-aspartic acid, L-aspartic acid, D-glutamic acid, L-glutamic acid, D-pyroglutamic acid, L-pyroglutamic acid, D-valine, L-valine, tosyl-L-phenylalanyl chloride, (+)-camphorsulfonic acid, (−)-camphorsulfonic acid, (+)-10-camphorsulfonyl chloride, (−)-10-camphorsulfonyl chloride, (−)-camphanic acid, (−)-camphanic chloride, N-(2-Carboxybenzoyl)-(−)-10,2-camphorsultam, N-(2-carboxybenzoyl)-(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric acid, (−)-camphanic chloride, N-(2-carboxybenzoyl)-(−)-10,2-camphorsultam, N-(2-carboxybenzoyl)-(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric acid, (1S,3R)-(−)-camphoric acid, (R)-(−)-1,1'-binaphthyl-2,2'-diyl hydrogen phosphate, (S)-(+)-1,1'-binaphthyl-2,2'-diyl hydrogen phosphate, (S)-5-allyl-2-oxabicyclo[3.3.0]oct-8-ene, (+)-MBF-OH dimer, (−)-MBF-OH dimer, or a combination thereof.

15. The process of claim 11, wherein the acylating agent comprises acetyl chloride, acetic anhydride, or a combination thereof.

16. The process of claim 11 wherein step c) occurs in a solvent at a temperature in the range of 0° C. to a reflux temperature of the solvent.

17. The process of claim 11, comprising step e) purifying levoketoconazole.

18. The process of claim 17, wherein the purifying levoketoconazole comprises contacting the product of the resolution agent and the levoketoconazole with one or more a purification solvent, an acid, and a base.

19. The process according to the claim 18 wherein wherein the purification solvent comprises water, an alcohol, a ketone, an ether, a nitrile solvent, an ester, a hydrocarbon, a chloro solvent, a polar-aprotic solvent, or a combination thereof.

20. The process of claim 18 wherein the acid comprises (−)-dibenzoyl-L-tartaric acid monohydrate, (+)-dibenzoyl-D-tartaric acid monohydrate, (−)-di-p-toluoyl-L-tartaric acid, (+)-dibenzoyl-D-tartaric acid, D-(−)-tartaric acid, L-(+)-tartaric acid, dimethyl L-(+)-tartrate, dimethyl D-(−)-tartrate, diethyl L-(+)-tartrate, diethyl D-(−)-tartrate, diisopropyl L-(+)-tartrate, diisopropyl D-(−)-tartrate, (2R,3R)-tartranilic Acid, (S)-(+)-2-butanol, (R)-(−)-2-butanol, (S)-(−)-2-methyl-1-butanol, (S)-(+)-2-octanol, (R)-(−)-2-octanol, (R)-(+)-1-phenylethyl alcohol, (S)-(−)-1-phenylethyl alcohol, (R)-(−)-1-phenyl-2,2,2-trifluoroethanol, (S)-(+)-1-Phenyl-2,2,2-trifluoroethanol, (R)-(−)-1-(9-anthryl)-2,2,2-trifluoroethanol, (S)-(+)-1-(9-anthryl)-2,2,2-trifluoroethanol, (R)-(−)-1-amino-2-propanol, (S)-(+)-1-amino-2-propanol, (−)-cis-2-benzylaminocyclohexanemethanol, (+)-cis-2-benzylaminocyclohexanemethanol, (R,R)-(+)-bis(α-methylbenzyl)amine hydrochloride, (S,S)-(−)-bis(α-methylbenzyl)amine hydrochloride, (1R,2R)-1,2-bis(2-hydroxyphenyl)-ethylenediamine, (1S,2S)-1,2-bis(2-hydroxyphenyl)-ethylenediamine, (R)-(+)-1-(4-bromophenyl)-ethylamine, (S)-(−)-1-(4-bromophenyl)-ethylamine, (S)-(−)-N,N-dimethyl-1-phenylethylamine, (R)-(+)-N,N-dimethyl-1-phenylethylamine, (S)-1-(4-Nitrophenyl)ethylamine hydrochloride ((S)-nitresolve), (R)-1-(2-naphthyl)ethylamine, (S)-1-(2-naphthyl)ethylamine, (S)-(−)-1-phenylethylamine, (R)-(+)-1-phenylethylamine, brucine anhydrous, cinchonidine, cinchonine, quinine, quinidine, (+)-dehydroabietylamine, (R)-(−)-N-(3,5-dinitrobenzoyl)-α-phenylethylamine, (R)-(+)-α-methylbenzylisocyanate, (S)-(−)-α-Methylbenzylisocyanate, (R)-(−)-1-(1-naphthyl)ethylisocyanate, (S)-(+)-1-(1-naphthyl)ethylisocyanate, (S)-(+)-α-methoxy-α-(trifluoromethyl)phenylacetyl chloride (MTPA-Cl), (R)-(−)-MTPA-Cl, (+)-menthyl chloroformate, (−)-menthyl chloroformate, methyl D-(−)-mandelate, methyl L-(+)-mandelate, (S)-(−)-N-(1-phenylethyl)-phthalamic Acid, (R)-(+)-N-(α-Methylbenzyl)-phthalamic Acid, (S)-(+)-α-methoxyphenylacetic acid, (R)-(−)-α-methoxyphenylacetic acid, (+)-MTPA, (−)-MTPA, (S)-(+) (γ-carboxy-γ-butyrolactone, (R)-(−)-γ-carboxy-γ-butyrolactone, (R)-(−)-hydratropic acid, (S)-(+)-hydratropic acid, D-(+)-malic acid, L-(−)-malic acid, (−)-menthoxyacetic acid, L-(+)-mandelic acid, D-(−)-mandelic acid, D-(−)-quinic acid, D-aspartic acid, L-aspartic acid, D-glutamic acid, L-glutamic acid, D-pyroglutamic acid, L-pyroglutamic acid, D-valine, L-valine, tosyl-L-phenylalanyl chloride, (+)-camphorsulfonic acid, (−)-camphorsulfonic acid, (+)-10-camphorsulfonyl chloride, (−)-10-camphorsulfonyl chloride, (−)-camphanic acid, (−)-camphanic chloride, N-(2-Carboxybenzoyl)-(−)-10,2-camphorsultam, N-(2-carboxybenzoyl)-(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric acid, (−)-camphanic chloride, N-(2-carboxybenzoyl)-(−)-10,2-camphorsultam, N-(2-carboxybenzoyl)-(+)-10,2-camphorsultam, N-(2-carboxy-4,5-dichlorobenzoyl)-(−)-10,2-camphorsultam, N-(2-carboxy-4,5-dichlorobenzoyl)-(+)-10,2-camphorsultam, (+)-camphoric Acid, (1S,3R)-(−)-camphoric acid, (R)-(−)-1,1'-binaphthyl-2,2'-diyl hydrogen phosphate, (S)-(+)-1,1'-binaphthyl-2,2'-diyl hydrogen phosphate, (S)-5-allyl-2-oxabicyclo[3.3.0]oct-8-ene, (+)-MBF-OH dimer, (−)-MBF-OH dimer, or a combination thereof.

21. The process of claim 18, wherein the base comprises an inorganic base, an organic base, or a combination thereof.

22. Crystalline levoketoconazole having a chiral purity about 99.5% by chiral HPLC.

23. The crystalline levoketoconazole of claim 22, wherein the chiral purity is greater than 99.85% by chiral HPLC.

24. The crystalline levoketoconazole of claim 22, wherein the chiral purity is greater than 99.99% by chiral HPLC.

25. The crystalline levoketoconazole of claim 22, wherein the crystalline levoketoconazole has a DSC onset temperature of 159.2° C.

26. Crystalline levoketoconazole having powder X-ray diffraction peaks at 17.4, 19.8 and 23.6±0.2°2θ and a purity greater than 99.0% by HPLC.

27. The crystalline levoketoconazole of claim 26 further comprising powder X-ray diffraction peaks at 10.4, 15.9, 18.7, 19.2, 20.3, 21.1 and 27.4±0.2°2θ.

28. The crystalline levoketoconazole of claim 26 having a powder X-ray diffraction pattern substantially as shown in FIG. 1.

29. The crystalline levoketoconazole of claim 26, wherein the crystalline levoketoconazole has a DSC onset temperature of 159.2° C.

30. The crystalline levoketoconazole of claim 26 wherein the crystalline levoketoconazole has a $d_{90}$ particle size distribution of less than or equal to 100 µm.

* * * * *